United States Patent [19]
Chang

[11] Patent Number: 5,519,218
[45] Date of Patent: May 21, 1996

[54] SAMPLE HOLDER FOR SPECTROSCOPY

[76] Inventor: On Kok Chang, 1031 Belvedere La., San Jose, Calif. 95129

[21] Appl. No.: 101,880

[22] Filed: Aug. 4, 1993

[51] Int. Cl.$^6$ ................................................. G01N 21/01
[52] U.S. Cl. ..................... 250/339.07; 250/343; 356/244
[58] Field of Search ..................................... 250/339, 576, 250/343; 356/440, 244

[56] References Cited

U.S. PATENT DOCUMENTS

| 2,068,476 | 1/1937 | Thomas | 356/70 |
|---|---|---|---|
| 4,135,100 | 1/1979 | Harada et al. | 356/440 |
| 4,575,246 | 3/1986 | Nishizawa et al. | 356/346 |
| 4,678,333 | 7/1987 | Anderson | 356/346 |
| 4,682,890 | 7/1987 | de Macario et al. | 356/244 |
| 4,684,255 | 8/1987 | Ford | 356/346 |
| 4,695,727 | 9/1987 | Brierley et al. | 250/339 |
| 4,740,082 | 4/1988 | Young | 356/346 |
| 4,799,001 | 1/1989 | Burch | 356/346 |
| 4,847,878 | 7/1989 | Badeau | 356/346 |
| 4,943,735 | 7/1990 | Nishikawa | 356/440 |
| 5,133,598 | 7/1992 | Badeau | 356/346 |

Primary Examiner—Carolyn E. Fields

[57] ABSTRACT

There is provided a sample holder for use in radiant spectroscopy analysis. The sample holder comprises a plurality of openings defined by one or more solid, substantially opaque, structural elements, each of the openings being arranged to retain a solid, semi-solid, gel or liquid material sample in the opening. Desirably, the openings constitute at least a major portion of the combined area of the one or more structural elements and the openings. In one embodiment, the sample holder comprises a plurality of strips secured together at irregular (random) or regular intervals. Desirably, one first group of strips is disposed in parallel spaced apart relation and a second group of strips disposed in parallel relation with the groups intersecting at an angle of between 30 and 150 degrees and secured together at substantially regular intervals. The strips may be woven as in wire mesh, or non-woven as in expanded metal. In another embodiment, the sample holder is a sheet of metal having perforations. In each embodiment, the sample holder is of structural elements which are substantially solid and opaque to infrared (IR) radiation. The void spaces or openings are defined by the structural elements (i.e. wires). The void spaces retain the sample to be analyzed by spectroscopy.

2 Claims, 8 Drawing Sheets

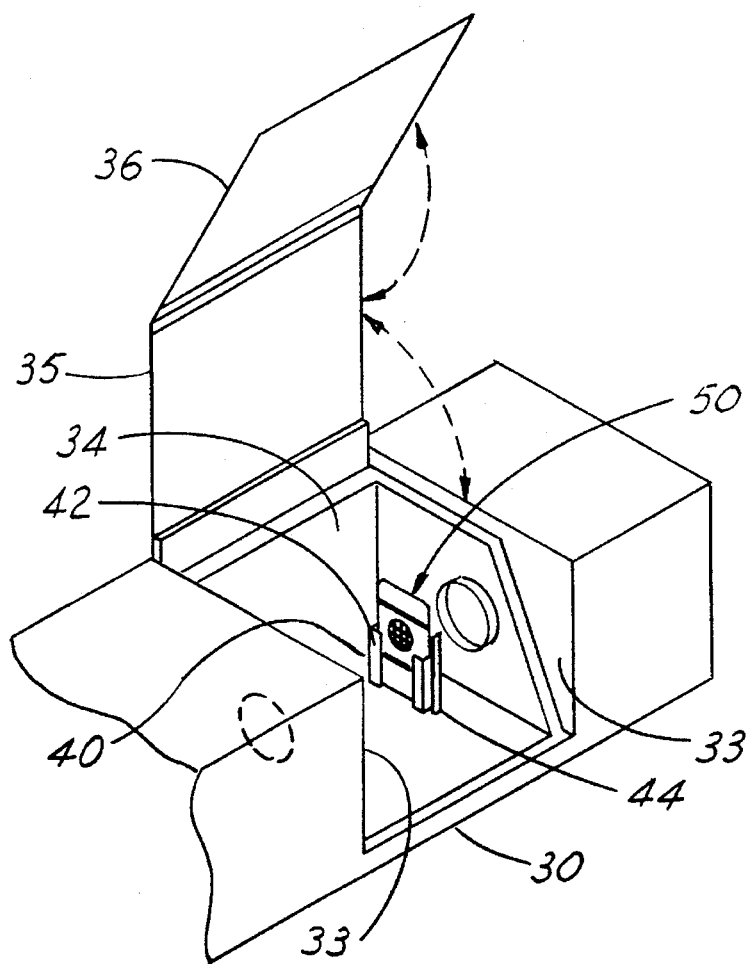
Fig. 3
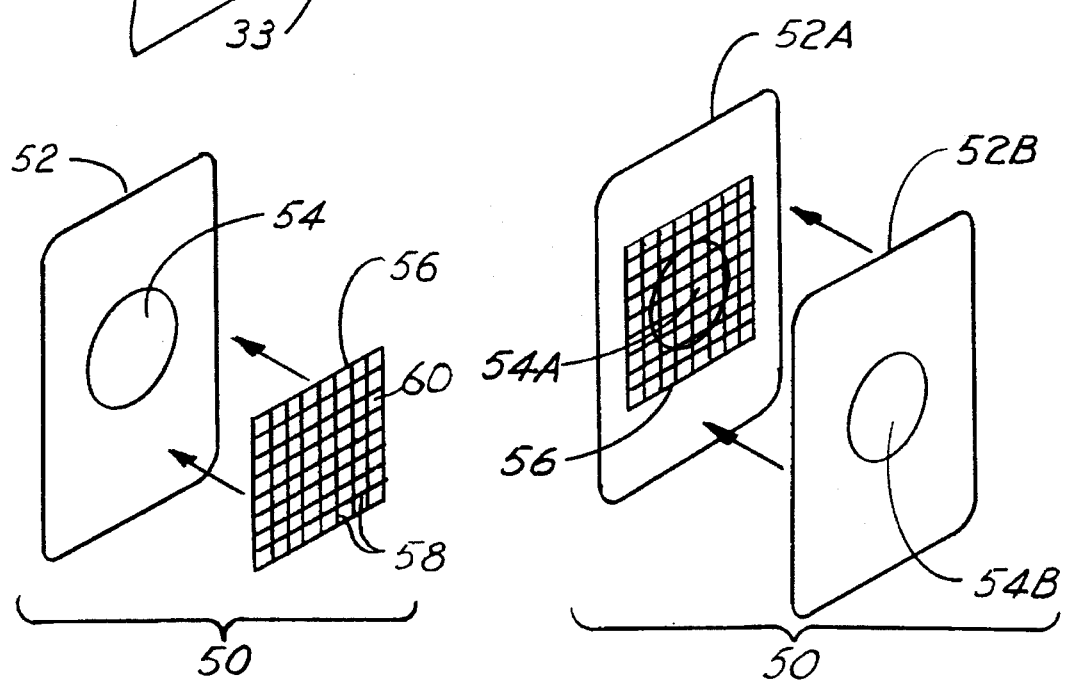
Fig. 4
Fig. 5

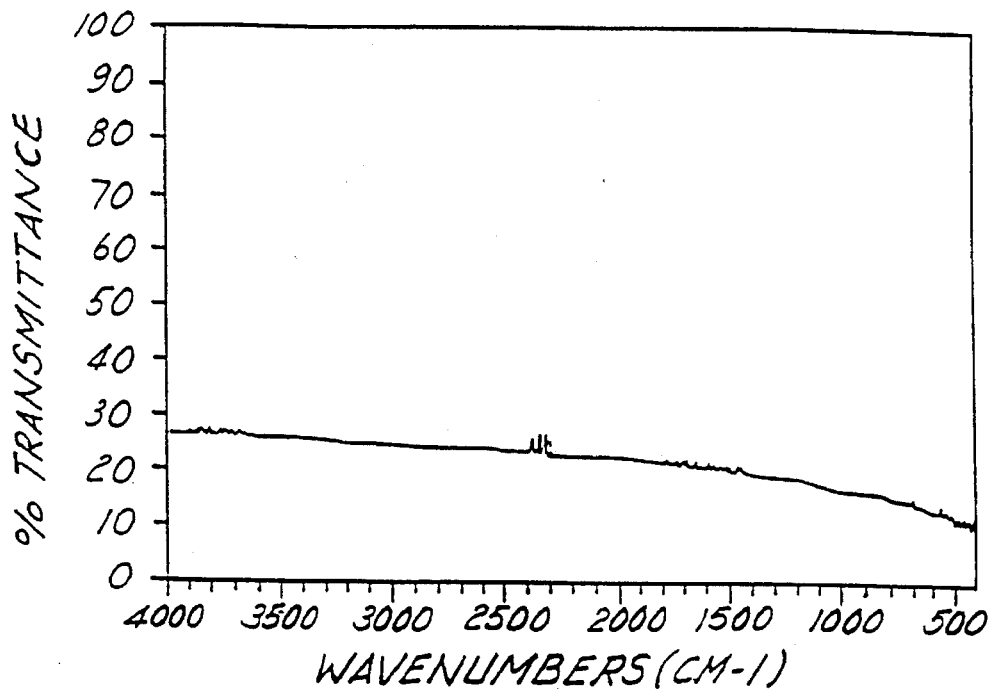
Fig. 15a
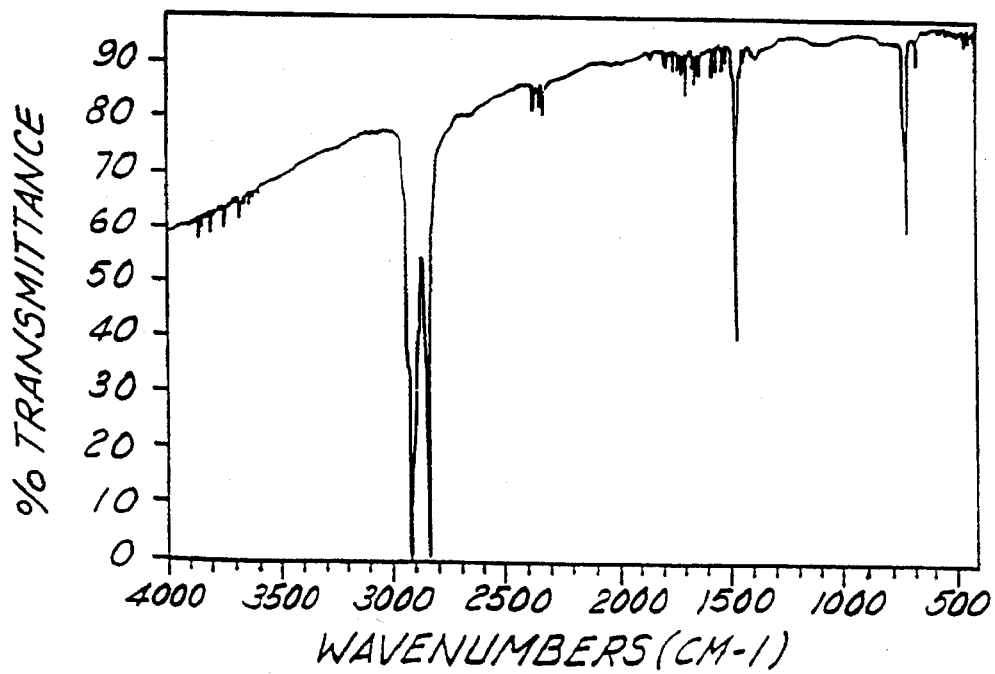
( PRIOR ART ) Fig. 15b

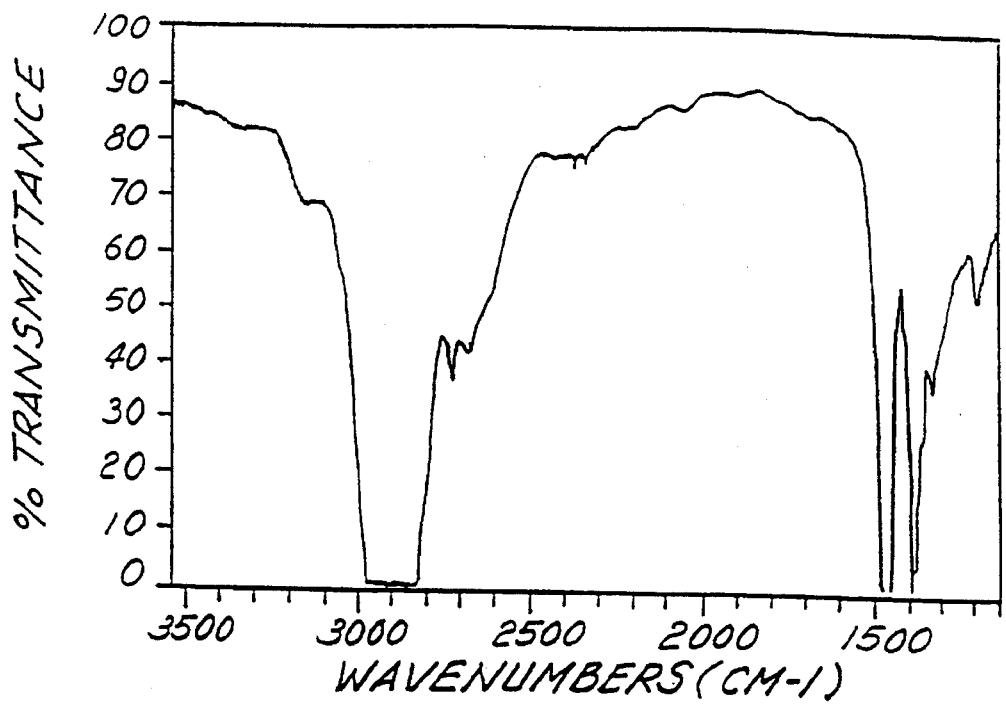
Fig. 16a
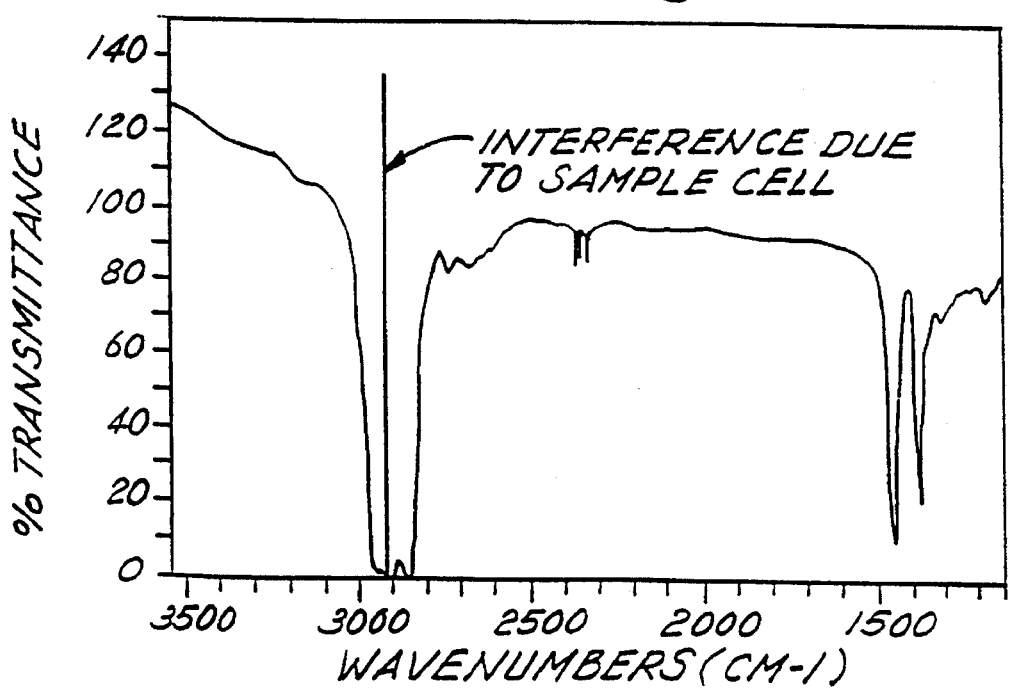
(PRIOR ART) Fig. 16b

SAMPLE HOLDER FOR SPECTROSCOPY

FIELD OF THE INVENTION

This invention pertains generally to the field of analytical instruments as exemplified by infrared spectrometers, Fourier Transform Infra-Red (FTIR) spectrometers including interferometric FT and dispersive spectrophotometers and particularly to sample holding apparatus therefore.

BACKGROUND OF THE INVENTION

In infrared spectrometers, a beam of radiation from a source is directed through a series of mirrors or other focusing elements onto a sample held in a holder. The radiation transmitted through or reflected from the sample is then collected and directed onto a detector. In a dispersive instrument, the polychromatic IR beam from the source first goes through a monochromator. The monochromatic IR beam then goes through the sample and reaches the detector. The wavelength of the monochromatic IR beam changes with time. The sample absorbs IR radiation of different wavelength to a different extent. The detector measures the intensity of the IR radiation as a function of wavelength. A spectrum is constructed from the data of intensity vs. wavelength or wave number. In FTIR spectroscopy, the output signal from the detector is analyzed with known computer processing techniques to derive information concerning the structure and composition of the sample. Spectrophotometers measure the relative intensities of light in different parts of a spectrum.

The primary advantages of FTIR spectrophotometers are that entire wavelength ranges can be analyzed faster, with more energy throughput and with reduced background stray light. Such advantages are well known in the spectrophotometer art and, consequently, have given rise to the increasing use of FTIR spectrophotometers.

Conventionally, spectrophotometers can be of either single beam or double beam variety. In a single beam instrument, the sample and a blank, which consists of, for example, a sample holder or a sample cell filled with a solvent, must be measured separately. The spectrum of the blank (reference) is then subtracted from the spectrum of the sample. It is often necessary to disrupt the control environment in order to switch from sample to blank measurement. Consequently, the blank measurement is neither simultaneous with the sample measurement nor is it performed under identical conditions.

As a means of avoiding this inaccuracy, double beam systems were developed and are well known in the art. In such systems, one beam is directed through the sample cell or sample material whereas a second beam, following a substantially identical optical path—except for that portion of the path passing through the sample—is introduced. Normally, this is accomplished by positioning, both before and after the sample cell, rotatable or otherwise movable mirrors, or other beam direction control optical elements. Accordingly, the incoming or incident beam directed to the sample cell is intermittently redirected along a path similar in length and other optical characteristics to that of the sample beam but which path does not contain a sample. Thus, by optically or electrically subtracting the signal representative of the incident beam having passed through the sample from the beam having passed through the reference path, a more accurate measurement is achieved. Even in a double beam system, noise created by conventional sample holders is a problem.

Many of the FTIR spectrometer systems in commercial and laboratory use today make use of a Michelson interferometer to create a time varying light wave to pass through a sample of material. Variations in the light intensity due to interference in the sample chamber are created by a moving mirror in the interferometer.

In a basic Michelson-type interferometer, the radiation flux emanating from a source of monochromatic light, either in the visible or the invisible regions of the electromagnetic spectrum, impinges on a beam splitter after passing through a collimator. The beam splitter is oriented at an angle of 45° to the direction of the incoming collimated beam so that a portion (i.e. percentage) of the impinging beam is transmitted without change of direction and a portion is reflected through a 90° angle. Each portion is reflected back towards the beam splitter by a beam reversing mirror, the return optical path being coincident with the forward path. At the beam splitter, recombination of the two portions takes place with the first now progressing in reflection and the second in transmission towards a common path leading to a light receiving device such as a photoelectric detector.

If a monochromatic source is used, and if the movable mirror referred to earlier is actually displaced a predetermined limit by mounting the mirror on an accurate scanning assembly following a strictly rectilinear path, the output of the photodetector will be a sine wave of much lower frequency compared with the monochromatic emission line of the source but with a constant peak-to-peak amplitude. If the Fourier Transform is computed, the resulting trace, in the form of a very narrow band, represents the emission line spectrum of the source.

If a broad-band infrared source is substituted for the monochromatic infrared source, the output of the detector when the scanning mirror is in motion will no longer be a pure sine wave since the spectrum of the source will include waves of different frequencies. Each of the optical sine waves will give rise to two constituent beams and one resultant beam of different frequencies will be represented in the instantaneous output of the detector, each by its own modulation sine wave of related frequency and amplitude. If the output of the detector is plotted as before, the trace that results represents the interferogram of the source. If a sample not opaque to infrared (IR) radiation is placed in the beam path, the waves of different frequencies present in the spectrum of the source are attenuated to a different extent in a manner that is characteristic of the chemical nature of the sample and the resulting interferogram represents the infrared absorption of the sample superimposed on the interferogram of the source.

By taking the Fourier Transforms of the two interferograms, thus obtaining independently the spectrum of the sample-cum-source and that of the source alone, and then determining the ratio of the first spectrum and the second, the spectrum of the sample is derived.

In typical spectroscopy instruments, a sample is held in position in a focused infrared beam by a holding fixture which, as described in U.S. Pat. No. 4,695,727, typically has a housing with walls defining a sample holder. Each of the end walls has an opening, an inlet opening on one wall and an outlet opening on the other wall, with the sample holder being disposed between the walls and positioned in the beam path so that the beam passes between the inlet and outlet openings and through the sample holder. The sample holder itself consists of two thin holding elements, often referred to as windows, which are joined together to hold the sample in place. One obvious requirement of the material for the window is that it be transparent to infrared (IR) radiation. Such transparent windows are pervious to radiation. Materials satisfying this requirement are mostly inorganic salts such as NaCl, KBr, CaF$_2$ and ZnSe. However, IR sample cells using these materials are too expensive to be disposable. An inexpensive disposable IR sample holder is marketed by 3M and is in the general form of a slide projector slide and is generally as described in U.S. Pat. No. 4,695,727. There is only one window. The window material is a porous polyethylene film. The sample to be measured is spread onto the window and is held in the pores of the polyethylene film. Because polyethylene has a unique IR spectrum, the absorption spectrum of the IR card typically interferes with the analysis of the sample. Although in principle the IR spectrum of polyethylene can be subtracted out, distortion of the spectrum usually still persists even in sophisticated interferometric spectrophotometers.

Therefore, what is needed is a new sample holder which retains a solid, semi-solid, gel or liquid sample without causing significant distortion of the spectrum.

SUMMARY OF THE INVENTION

There is provided a sample holder for use in radiant spectroscopy analysis. The sample holder comprises a plurality of openings defined by one or more solid, substantially opaque, structural elements, each of the openings being arranged to retain a solid, semisolid, gel or liquid material sample in the opening. Desirably, the openings constitute at least a major portion of the combined area of the one or more structural elements and the openings. In one embodiment, the sample holder comprises a plurality of strips secured together at irregular (random) or regular intervals. Desirably, one first group of strips is disposed in parallel spaced apart relation and a second group of strips disposed in parallel relation with the two groups intersecting at an angle of between 30 and 150 degrees and secured together at substantially regular intervals. It is preferred that the angle be close to 90 degrees as the open area (void space) is largest at 90 degrees. The strips may be woven as in wire mesh, or non-woven as in expanded metal. In another embodiment, the sample holder is a sheet of metal having perforations. In each embodiment, the sample holder is of structural elements which are substantially solid and opaque to infrared (IR) radiation. The void spaces or openings are defined by the structural elements (i.e. wires). The void spaces retain the sample to be analyzed by spectroscopy.

In the method of the invention, the sample holder is used with a typical spectroscopic apparatus having a source for generating a beam of radiation of pre-selected spectral wavelengths and a means for focusing an image of the source means and directing the beam so as to define an optical path through a sample position. A preferred sample holder in the sample position comprises an open mesh wire screen having a plurality of openings for retention of a solid, semi-solid, gel or liquid material sample in the openings by adhesion between the material and the wires of the screen and/or compression of the material between the wires. There are also photosensitive detector means and means for receiving the beam of radiation from the sample position and focusing the beam on the detector. The sample holder is particularly useful for retaining a semi-solid or gel sample by adhesion between the sample and the solid structural elements of the sample holder. Liquid samples are likewise retained by adhesion and surface tension. Solid samples are held by adhesion and compression between the structural elements. The structural elements do not cause significant distortion of the spectrum.

These and other objects, features and advantages will become apparent from the following description of the preferred embodiments, appended claims and accompanying drawings.

BRIEF DESCRIPTION OF THE DRAWINGS

FIG. 3 is a perspective view of a sample chamber with a cover open.

FIG. 4 is a perspective view of one embodiment of a sample holder according to the invention.

FIG. 5 is a perspective view of a preferred embodiment of a sample holder according to the invention.

FIG. 15a shows a transmission spectra of a nickel wire screen sample holder according to the invention.

FIG. 15b shows a transmission spectra of a conventional 3M IR disposable card sample holder having a polyethylene window.

FIG. 16a shows a transmission spectra of mineral oil tested on a nickel wire screen.

FIG. 16b shows a transmission spectra of mineral oil on a conventional 3M IR disposable card.

DETAILED DESCRIPTION OF THE PREFERRED EMBODIMENTS

Figure 1:
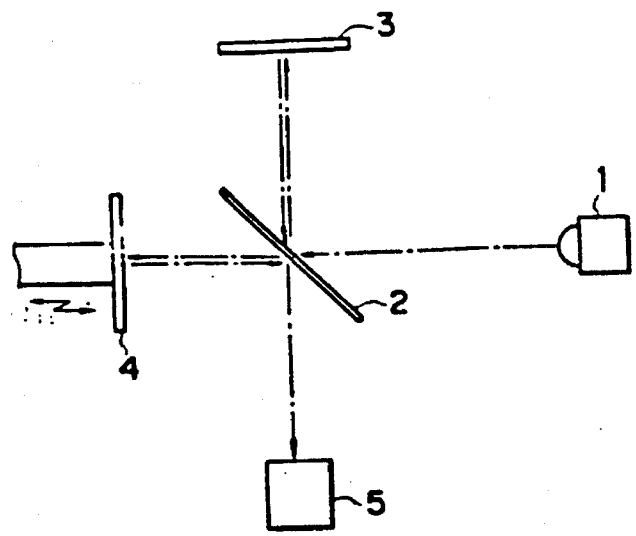
FIG. 1 is a diagrammatic plan view of a general layout of a FTIR spectrophotometer system.
Figure 2:
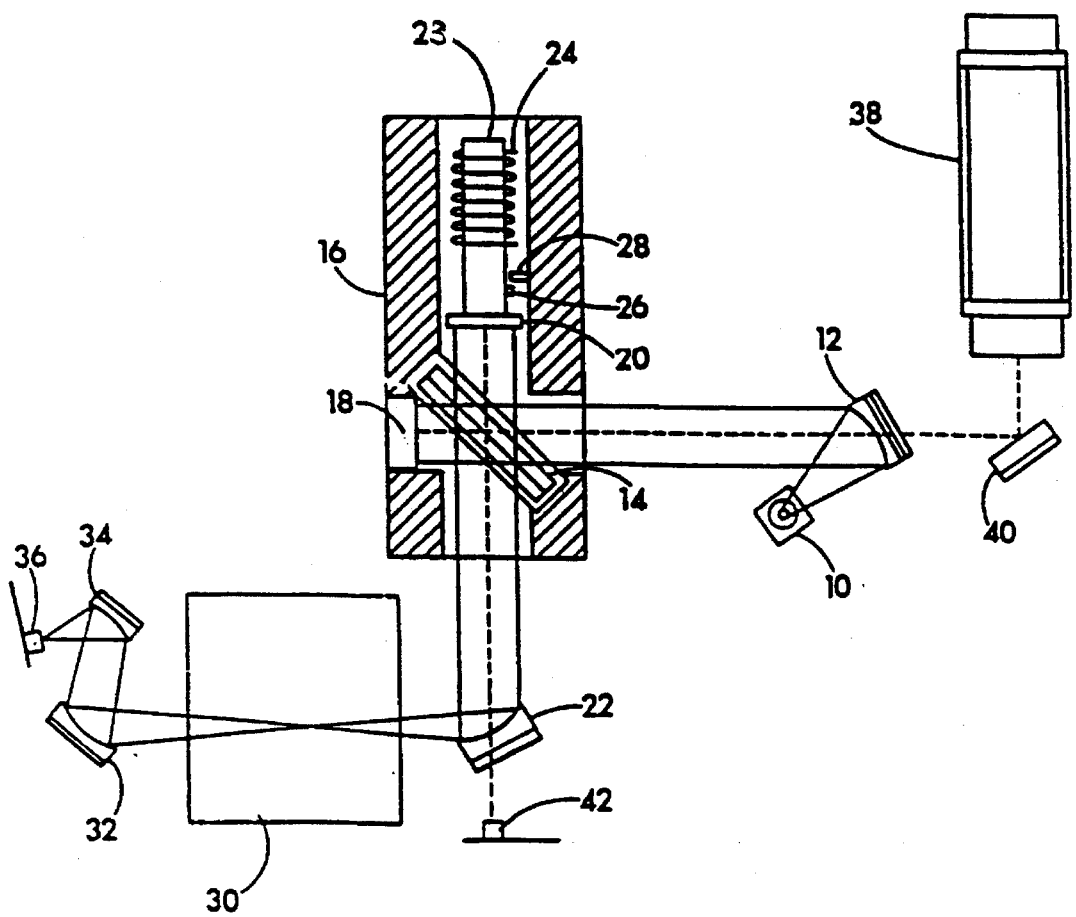
FIG. 2 is a schematic plan view of a FTIR spectrophotometer system.

The general layout of a typical FTIR spectrophotometer system utilizing a Michelson interferometer is as shown in FIGS. 1 and 2. The principle of the system will be briefly described with reference to FIG. 1. The system is as illustrated in schematic form in FIG. 2. It is to be understood that such systems can be laid out in many geometries and that the schematic illustrations of FIGS. 1 and 2 are intended to be exemplary.

Interferometric Spectrophotometers Optical Analytical Instrument

The Michelson interferometer is an interferometer in which light from a source 1 strikes a beam splitter 2 at an angle of 45° where light is divided into two light beams, one reflected and one transmitted by the splitter 2. The reflected beam is directed to a stationary mirror 3 and reflected thereby, the transmitted beam is directed to a movable mirror 4 and reflected thereby, and the beams are then recombined by the beam splitter 2 to enter a detector 5 where interference fringes are formed due to the difference between the beam paths. In carrying out Fourier Transform spectroscopy, the movable mirror is continuously moved at a predetermined constant speed in a direction toward and away from the beam splitter. The detector responds to the continuously varying interference fringes to produce an AC signal (interferogram) which is Fourier Transformed by means of a computer. Provided that the movable mirror is moved at a predetermined constant speed v, the beam path difference x becomes a function of time t, that is, x=2 vt, and therefore, the output of the detector also becomes a function of time. A light component having a wave number y is converted into an AC signal having a frequency f2 vy Hz.

It is to be noted that the sample to be analyzed is generally located in that portion of a beam path along which a light beam travels from the beam splitter 2 to the photodetector 5. In order to compare the sample with the reference materials, the beam path from the beam splitter 2 to the photodetector 5 is generally divided into two beam paths, and a cell filled with the sample is inserted in one beam path and a cell filled with the reference material is inserted in the other beam path.

An infrared light source is indicated at 10 of FIG. 2. The light emanating from the light source 10 is reflected off of a collimating mirror 12 which directs the light in a beam toward a beam splitter 14, located in an interferometer housing 16. The light from the mirror 12 which passes through the beam splitter 14 is then reflected by a reflecting mirror 18 located in the optical path of the beam coming from the mirror 12. Perpendicular to the light path between the mirrors 12 and 18 is a light path created by recombining light from the first beam with light partially reflected by the beam splitter 14. This path extends between a moving mirror 20 and a focusing mirror 22. The moving mirror 20 moves toward and away from the beam splitter 14, or vertically as viewed in the schematic view of FIG. 2. This motion is accomplished by mounting the moving mirror 20 on a shaft 23 which is reciprocated on a linear axis forwardly and rearwardly by a coil 24. Mounted on the shaft 23 is a projection or tab 26 which is arranged so as to pass through a light beam extending between a light source and a photodetector 28 as the shaft moves linearly in the housing 16 so as to interrupt the light flow to the photodetector 28 when the tab 26 is adjacent thereto.

Light leaving the interferometer housing 16 is reflected by the focusing mirror 22 through a sample chamber 30 from where it goes to focusing mirrors 32 and 34 in which it is focused on a detector 36. Motion of the moving mirror 20 thus makes a time dependent light signal in the sample chamber 30, the variations in which may be detected by the detector 36. This information can be analyzed by appropriate Fourier analysis to indicate the spectral characteristics of the substance contained in the sample chamber 30.

Optical analytical instruments particularly of the preferred Michelson interferometer type used in Fourier spectroscopy (spectrophotometers) are further described in U.S. Pat. Nos. 4,575,246, 4,678,333, 4,684,255, 4,695,727, 4,740,082, 4,799,001, 4,847,878 and 5,133,598, each of which is incorporated herein by reference in its entirety. It should be noted that the 333, 727, 001, 878 and 598 patents are assigned to the Nicolet Instrument Corporation of Madison, Wisconsin. A Nicolet model Magna-IR System 750 infrared spectrometer with a spectral range covering about 4,800 to about 400 $cm^{-1}$ and with a rapid scanning interferometer capable of better than 0.1 $cm^{-1}$ resolution was used in the experiments which are described herein below.

Sample Chamber for Optical Analytical Instruments

The sample chamber 30 is shown in greater detail in FIG. 3. The sample chamber 30 is defined by side walls 33, a back wall 34, a cover 35 and a front wall 36 formed by cover 35. Within sample chamber 30 is mounted a retainer 40 having pairs of upright members 42 and 44 between which sample holder 50 of the invention is received.

Sample holder 50 comprises a self supporting rigid support 52, preferably of stiff cardboard. (FIG. 4). The support 52 is constructed and arranged to be slidably received between uprights 42 and 44. The stiff support 52 has an opening 54 preferably centrally located. A sample retaining means in the form of a matrix 56 mounted by adhesion or the like in the opening 54 retains the sample to be analyzed.

In one embodiment, the support 52 may be eliminated and the sample holder itself may be entirely constructed as a self-supporting matrix 56, of a size sufficient to seat between uprights 42 and 44. In a preferred embodiment, as shown in FIG. 5, the matrix 56 is retained between two rigid supports 52A, 52B. Each support 52A, 52B is in the form of a panel with a central opening 54A, 54B to define an open area through which the infrared beam passes. Conventional adhesive is used to mount the matrix 56 to a support (i.e. 52A) and to join pairs of supports 52A, 52B together.

The matrix portion 56 of sample holder 50 which retains a solid, semi-solid, gel or liquid material may be arranged in a variety of configurations. In its simplest form, the matrix 56 comprises a plurality of solid strips 58 arranged to form a plurality of openings 60 for retention of a solid, semi-solid, gel or liquid material sample in the openings 60 by adhesion between the material and the strips 58, and/or compression of the material between the strips 58. Thus the strips 58 define void spaces or openings 60 which retain the sample and permit passage of light. At the same time, the spectral analysis is not distorted by the matrix 56 because it is of a material, which is opaque to infrared radiation.

Preferably, each of the strips 58 has a thickness less than the size of any one of the openings 60. The strips 58 are secured together at irregular or random intervals, preferably at points of crossing. The strips 58 may be secured together at substantially regular intervals, by weaving together or welding or stamping together or crimping cross layers of strips. In one configuration, the strips 58 comprise a first group of strips 58A disposed in parallel spaced apart relation and a second group of strips 58B disposed in parallel spaced apart relation with groups 58A and 58B intersecting at an angle of between about 75 and about 105 degrees and secured together at substantially regular intervals. Preferably, the angle of intersection is 90 degrees at intervals constituting points of crossing. Preferably, the first group is laid over the second group in transverse relation, set crosswise at about 75 to about 105 degrees.

Figure 6:
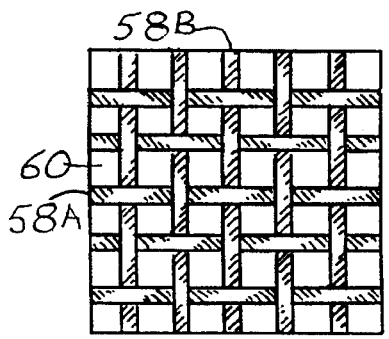
FIG. 6 is a frontal view of a portion of a sample holder with a plain weave configuration.
Figure 7:
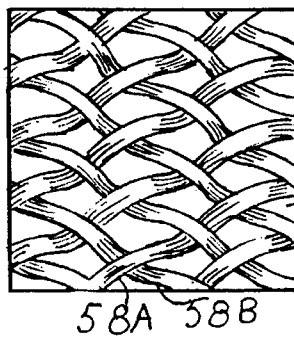
FIG. 7 is a perspective view of a portion of a sample holder with a plain weave configuration.
Figure 8:
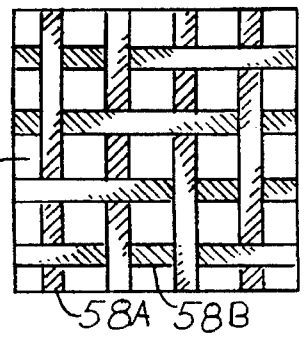
FIG. 8 is a frontal view of a portion of a sample holder with a twilled weave configuration.
Figure 9:
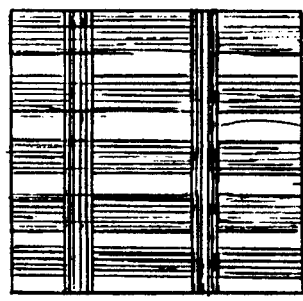
FIG. 9 is a frontal view of a portion of a sample holder with a weave pattern where a first set and a second set of strips are of different size.
Figure 10:
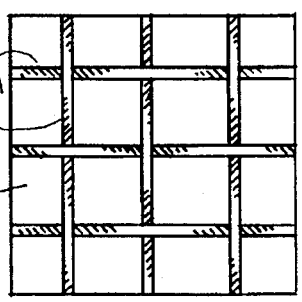
FIG. 10 is a frontal view of a portion of a sample holder with a grid configuration utilizing very fine wire providing a high percentage of open area.
Figure 11:
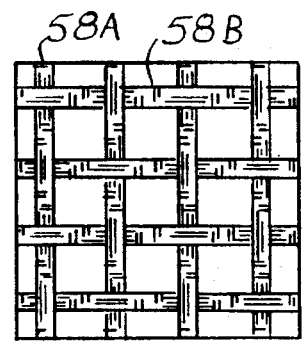
FIG. 11 is a close-up frontal view of a portion of a sample holder with a plain weave configuration having deep crimps at each joint or wire intersection.

If the strips are woven together, as in a mesh, several configurations are possible. In the preferred configuration, a first group of wires 58A passes alternately over and then under a second group of wires 58B disposed at right angles to the first. This is essentially a plain weave. (FIGS. 6 & 7). In a second configuration, sometimes referred to as a twilled weave, each wire of the first group 58A alternately goes over two wires of the second group 58B and then under two wires of the second group where the two groups of wires are disposed at essentially right angles. (FIG. 8). If desired, one group of wires may be thicker than the other. (FIG. 9). It is preferred that an essentially square grid configuration be used as the matrix for retaining the sample where a plain weave is used in cooperation with very fine wires, thus producing a very high percentage of open area on the order of up to 95%. (FIG. 10). It is preferred to have deep crimps 57 in the wires at the points of joinder or intersection to lock the weave. (FIG. 11).

Figure 12:
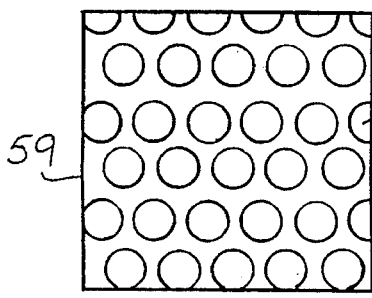
FIG. 12 is a frontal view of a portion of a sample holder with a perforated sheet metal construction
Figure 13:
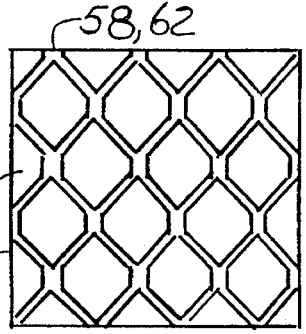
FIG. 13 is a frontal view of a portion of a sample holder with an expanded metal-type configuration.

Alternatively, it may be desired to have all of the strips disposed essentially in a common plane, non-woven, and forming a grid secured together at points of intersection, such as a retaining matrix 56 formed of perforated metal 59, with perforations forming the openings 60. (FIG. 12). Another non-woven grid may be formed from strips where each one of the strips 58 comprises a plurality of segments 62, some of which protrude outward from a common plane of the grid and are secured together at regular or irregular intervals and where some of the segments are twisted. Such twisted segments are formed from expanded metal and called expanded metal 64. (FIG. 13).

Figure 14:
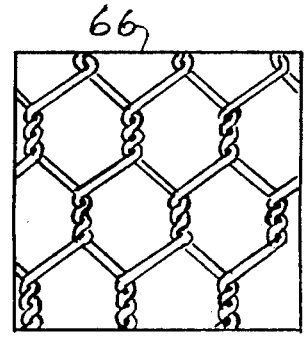
FIG. 14 is a frontal view of a portion of a sample holder with a twisted wire or "chicken wire" type construction.

Any combination of the above matrix patterns may be used, such as combining plain weave and heavier and lighter groups of wires, and crimping, galvanizing or welding to secure the pattern. The strips 58 may even be wound, wrapped or twisted together in a chicken wire pattern 66 forming openings 60 having a six-sided hexagonal shape. (FIG. 14).

Good results were obtained using a mesh woven screen formed of nickel wire as the matrix 56. The nickel wire size was about 0.03 mm in diameter with a mesh size of about 100 openings per linear centimeter or about 250 openings per linear inch. The open area is about 50% of the total area. It is desired to have an open area of about 80%, preferably 90% and most preferably 95%. The fine mesh metal wire screen of nickel can be used as an infrared cell or sample holder for low vapor pressure liquids and solids. The nickel screen has no absorption spectrum because the metal wire is totally opaque to the infrared radiation. When the screen is wetted by a liquid, the liquid is held in the space between the wires. A solid powder can also be pressed into the openings of the screen. The wire screen can thus be used as a sample holder for infrared spectroscopy. The use of a matrix in the form of a nickel wire screen was compared to conventional sample holders of two types. One was a conventional disposable infrared sample card, manufactured by 3M, which has polyethylene material retaining the sample to be analyzed. Another was a sample card having AgCl (silver chloride) as the material which forms the window of such conventional sample cell.

A sample of mineral oil was applied to a disc formed of AgCl and then another disc of AgCl was placed on top of it so that the space between the two AgCl discs holds the liquid in place by capillary action. In essence, the sample was sandwiched between the AgCl discs. This sandwich was then placed in the beam path to obtain a spectrum. The same type of procedure was used with the conventional sample cell having polyethylene as the material of the disc.

FIG. 15a shows the spectrum of the mesh screen of the invention. FIG. 15b shows the spectrum of a conventional slide having polyethylene as the window material. In FIGS. 15a and 15b, there is no sample in the holders. As can be seen, the polyethylene window material itself has an infrared spectrum. The infrared absorption of the polyethylene card would obviously interfere with the analysis of the sample were one retained therein. FIG. 16a shows the spectrum of mineral oil on the sample retaining mesh screen matrix of the invention. FIG. 16b shows the spectrum of the mineral oil retained on a conventional polyethylene sample holder. The noises at 3600 to 4000 per centimeter (FIG. 15b) and 1450 to 1750 per centimeter were due to water vapor and air. The noises at 2320 to 2370 per centimeter were due to carbon dioxide and air. As can be seen in FIG. 16b, there is a vertical line indicated by an arrow caused by the incomplete subtraction of the spectrum of the conventional sample cell itself which interferes with reading accuracy. The sample mineral oil layer retained on the nickel wire screen was actually thicker than the amount of sample able to be retained in the disposable infrared polyethylene sample card. That is why the transmittance of the whole spectrum is lower on the nickel screen than on the conventional card. The two spectrum are quantitatively nearly identical, however, and the nickel screen provides the advantage of having no interference caused by incomplete substraction of the sample holder's spectrum.

Figure 17:
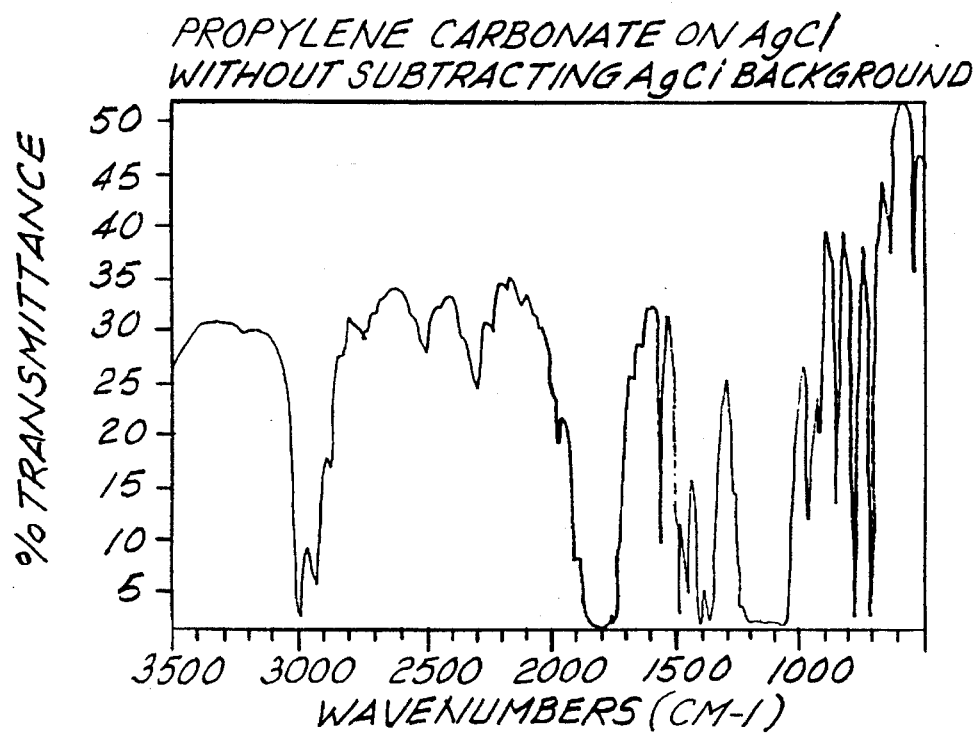
FIG. 17 is a transmission spectrum for a propylene carbonate sample tested on a disposable card having a window of AgCl; the transmission of the AgCl background being included.
Figure 18:
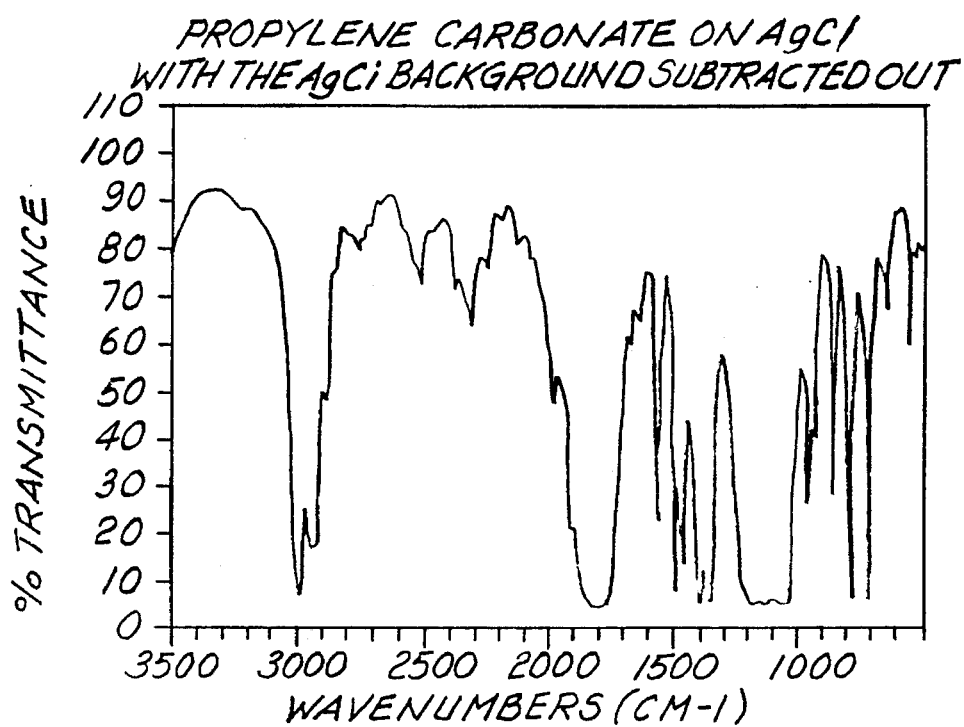
FIG. 18 is a transmission spectrum for a propylene carbonate sample tested on a disposable card having a window of AgCl; the transmission of the AgCl background being excluded or subtracted out.
Figure 19:
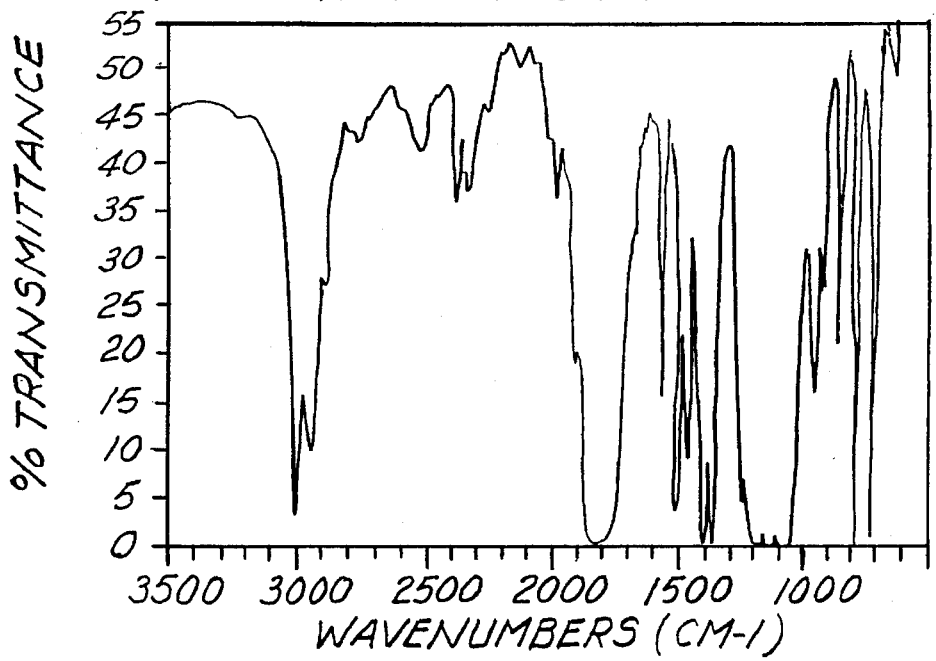
FIG. 19 is a transmission spectrum for a propylene carbonate sample tested on a nickel wire screen; the transmission of the wire screen being excluded or subtracted out.
Figure 20:
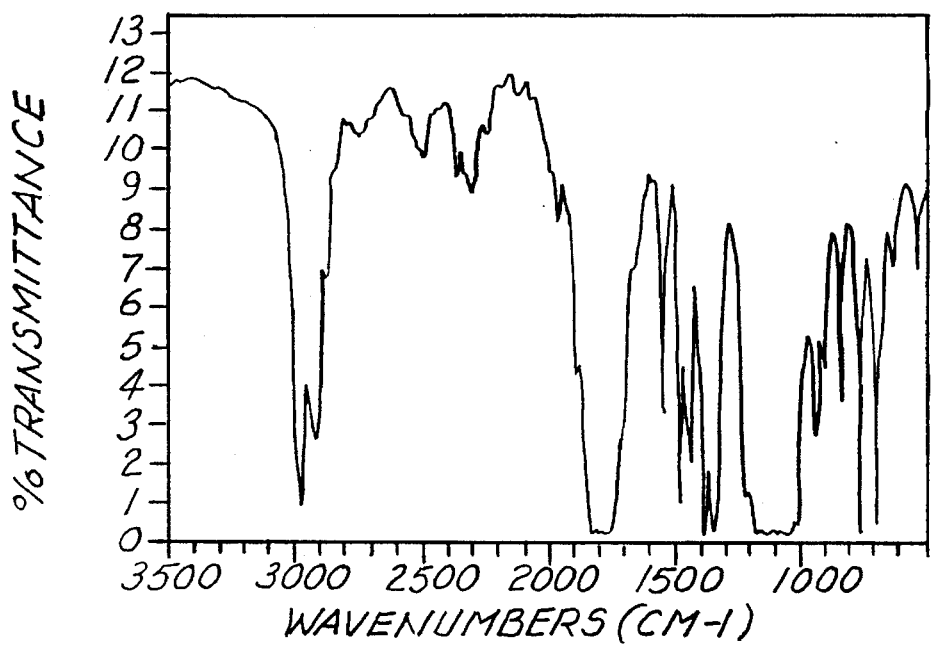
FIG. 20 is a transmission spectrum for a propylene carbonate sample tested on a nickel wire screen; the transmission of the wire screen being included.
Figure 21:
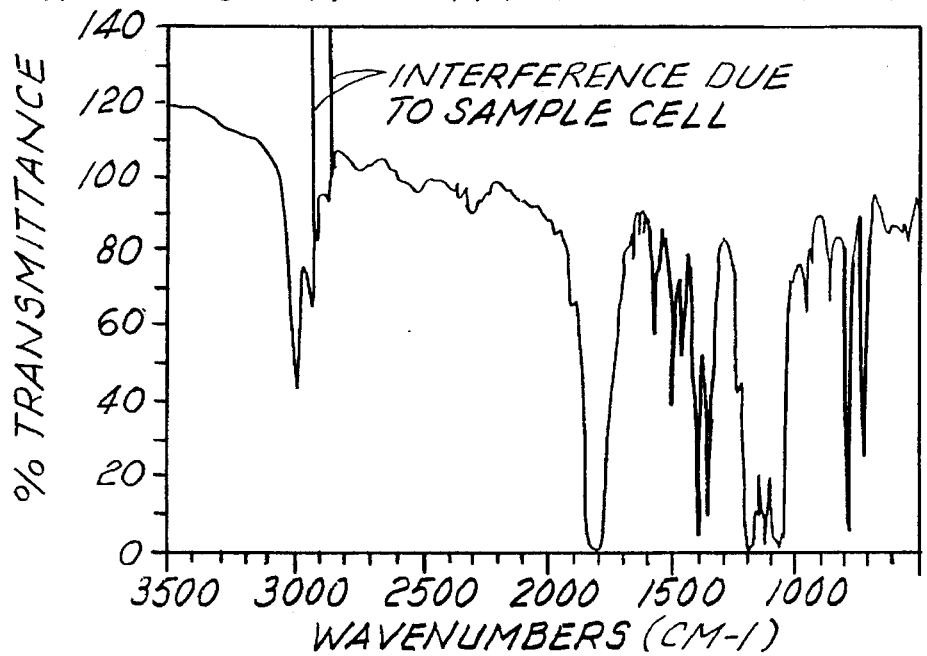
FIG. 21 is a transmission spectrum for a propylene carbonate sample tested on a 3M disposable card; the transmission of the card being excluded or subtracted out.
Figure 22:
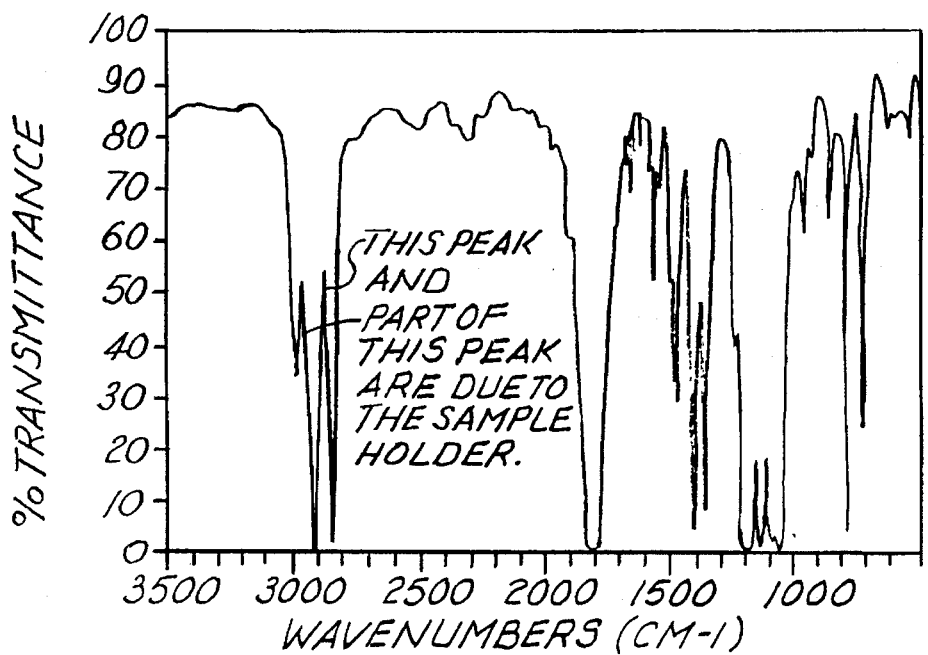
FIG. 22 is a transmission spectrum for a propylene carbonate sample tested on a 3M disposable card; the transmission of the card being included.

Additional comparisons were made using polyethylene carbonate as the sample and analyzing the spectrum of such sample on a conventional sample holder having a window formed of AgCl. The spectrum comparison using AgCl was performed both with inclusion of the AgCl background and by subtracting out the AgCl background. Correspondingly, a spectrum of propylene carbonate on the nickel screen was obtained with the nickel screen subtracted out and with the spectrum of the nickel screen included. The same series of tests were done with propylene carbonate on a conventional sample card having a window of polyethylene rather than AgCl (AgCl data is in FIGS. 17 & 18; nickel screen data is in FIGS. 19 & 20; and polyethylene window data is in FIGS. 21 & 22). The nickel screen sample holder yields results comparable to, and at least as good as, the very expensive AgCl based sample holder and the nickel screen gives results far superior to the conventional polyethylene-based sample holder. Given that the nickel screen sample holder would be as economical as, if not cheaper than, the polyethylene-based window, it is clear that the nickel mesh screen of the invention provides a significant advantage over conventional sample cell technology.

The screen or grid has no absorption spectrum because the metal wire is substantially or totally opaque to IR. Since the solid members of the matrix are not pervious to IR energy, they do not interfere with the spectral analysis of the sample. The sample screens of the invention are preferably formed of metallic material such as nickel, steel, galvanized and stainless steel, copper, aluminum, brass and bronze. If desired, more expensive metals may be used such as gold, tungsten and titanium. The material may be woven or non-woven and may have openings at regular or random intervals. This is not critical. It is only required that the openings be straight-through openings so that an infrared beam is able to pass directly through the openings. Thus, although the openings may be staggered in a given plane, the openings should all be within a given plane and not staggered, for example, in layers. Thus, it is possible to prepare a non-woven matrix by randomly laying down metal fibers in a common plane and then adhering the fibers together providing a random array of openings which are through-openings. A paper-type material where through-openings are not provided would not be suitable. Therefore, the matrix of the invention must provide thin, small diameter members or supports which define void spaces, passages or openings to hold the sample and to permit light to shine through. Preferably the matrix sample holder is constructed so that the area occupied by the openings represents a major portion of the total combined area of the openings and supporting matrix material.

Although not wishing to be held to any particular theory, the following is thought to apply. If the sample to be retained in the matrix is a liquid, it is retained by capillary action. Therefore, when the screen is wetted by a liquid, the liquid is held in the space between the wires. Theoretically, the lower the vapor pressure of the liquid to be analyzed the better will be the results; otherwise the liquid will tend to evaporate. Smaller openings will provide better results for lower surface tension liquids. Those skilled in the art will understand that the invention depends on capillary action which involves surface tension and capillary attraction which is the force of adhesion between the matrix elements, i.e. strips or wires, and the liquid or solid retained between the wires. Therefore, the force of adhesion, which is the molecular attraction exerted between surfaces of bodies in contact, is important to retaining samples between elements (wire, strips) of the grid. In the case of solid samples, there will be some compressive force which assists in retaining the solid in the grid. In some cases, a solid sample may be dissolved in a solvent, then the solvent applied to the matrix and dried. When the solvent dries, it leaves behind tiny crystals of the solid sample in the openings.

It should be remembered that if the openings in the screen are too large, the capillary action may not be sufficient to hold a liquid sample in place, causing the liquid sample to drip down. So, the size the openings will depend on the viscosity of the sample material as well as the surface tension and density; although surface tension is probably the most important. Typical measurements can take place from within about 30 seconds from the time a sample is applied. If the mesh size is small enough, surface tension will hold the sample in place except that liquid samples would tend to slowly evaporate. Therefore, the invention is able to be successfully utilized since the viscosity effect will tend to hold the liquid sample in place for a time sufficient to perform the spectral analysis despite the presence of the forces of gravity. This assumes that the sample is in a generally vertical position. Most of the infrared spectrometers on the market today have the IR beam in an essentially horizontal position so the sample is typically held in the vertical position. Accordingly, the IR beam will go through the mesh at an angle of about 90°. The screen of the invention could, however, be used in any orientation, horizontal or vertical.

While this invention has been described in terms of certain embodiments thereof, it is not intended that it be limited to the above description, but rather only to the extent set forth in the following claims.

The embodiments of the invention in which an exclusive property of privilege is claimed are defined in the appended claims.

I claim:

1. An instrument for the spectroscopic analysis of a sample material having means for transmitting an infrared (IR) beam along a beam path to an infrared detector, a sample holder positioned in the beam path, the sample holder consisting essentially of one or more metallic structural elements constructed as a matrix, said sample holder being supported by a pair of upright supports mounted on said instrument in said beam path for holding said matrix in place in said beam path, said one or more structural elements defining a multiplicity of completely void openings adapted to retain a solid, semi-solid, gel or liquid sample material therein, said one or more structural elements being opaque to infrared radiation, and said matrix lying between said uprights of said instrument in a plane at an angle of 90° to the direction of said beam, and wherein the matrix has about 100 openings per linear centimeter.

2. An instrument for the spectroscopic analysis of a sample material having means for transmitting an infrared (IR) beam along a beam path to an infrared detector, a sample holder positioned in the beam path, the sample holder consisting essentially of one or more structural elements constructed as a matrix, said sample holder being supported by a pair of upright supports mounted on said instrument in said beam path for holding said matrix in place in said beam path, said one or more structural elements defining a multiplicity of completely void openings adapted to retain a solid, semi-solid, gel or liquid sample material therein, said one or more structural elements being opaque to infrared radiation, and said matrix lying between said uprights of said instrument in a plane at an angle of 90° to the direction of said beam, and wherein the openings are defined by a plurality of said structural elements arranged in first and second groups with the structural elements of the first group in cross relation to the structural elements of the second group.

* * * * *